US00PP09334P

United States Patent [19]

Jessel, Jr.; Walter H.

[11] Patent Number: Plant 9,334

[45] Date of Patent: Oct. 17, 1995

[54] CARNATION PLANT NAMED 'CFPC SUGARPLUM'

[75] Inventor: Walter H. Jessel, Jr., Salinas, Calif.

[73] Assignee: California Florida Plant Company, L.P., Salinas, Calif.

[21] Appl. No.: 315,131

[22] Filed: Sep. 29, 1994

[51] Int. Cl.[6] ..... A01H 5/00

[52] U.S. Cl. ..... Plt./70.2

[58] Field of Search ..... Plt./70.1, 70.2

*Primary Examiner*—James R. Feyrer

*Attorney, Agent, or Firm*—Christie, Parker & Hale

[57] ABSTRACT

A new dwarf carnation plant suitable for growing in pots producing flowers of purple-flushed lavender coloration.

1 Drawing Sheet

SUMMARY OF THE INVENTION

The present invention relates to a new and distinct dwarf variety of carnation plant which was originated by me in a controlled breeding program by my crossing as seed parent the variety known as 'Peachy' and as pollen parent the variety known as 'Claret Elegance'. The varietal denomination of this new carnation is 'CFPC Sugarplum'.

Among the novel combination of characteristics possessed by the new variety which distinguishes it are dwarf growth habit not requiring application of growth retardants, tolerance to temperatures as high as 120° F. and as low as 10° F. and ability to produce flower buds that will open in a home environment with moderate light conditions. Flowers of the new variety are of an attractive purple-flushed lavender coloration.

Asexual reproduction by propagation by side shoot cuttings of the new variety as performed in Salinas, Calif., shows that the foregoing and other distinguishing characteristics come true to form and are established and transmitted through succeeding propagations.

Unlike preceding pot carnations, i.e., Lillipots (Sakata), Rocky Mountain Series (Goldsbury C.S.U.), and Knight Series (Goldsmith Seed Co.), CFPC pot carnations were selected and bred from indoor cut-types and are best grown under cover. The Lillipots, etc. were bred from outdoor garden-types and species and are best grown outdoors. The CFPC pot varieties are dwarf due to a homozygous recessive dwarfing gene. If crossed to the aforementioned "pot-types", the resultant progeny returns to tall cut seedlings.

The Lillipots are Knight Series are seed crops. The Rocky Mountain and European pot varieties (cuttings) are no longer commercially available.

BRIEF DESCRIPTION OF ILLUSTRATION

The accompanying illustration shows typical specimens of the vegetative growth and flowers of the new variety depicted in color as nearly true as it is reasonably possible to make the same in a color illustration of this character. Although propagation by side shoot cuttings is described, other known methods of asexual reproduction may also be used to reproduce 'CFPC Sugarplum'.

DESCRIPTION OF THE NEW VARIETY

The following is a detailed description of my new variety, with color terminology in accordance with The Royal Horticultural Society Color Chart (RHSCC). The terminology used in color description herein refers to plate numbers in the aforementioned color chart. Color designations and color descriptions may deviate from the stated values depending upon varying environmental, seasonal and cultural conditions.

The information provided herein is based on observations of plants grown inside commercial greenhouses at Salinas, Calif. The height of plant and flower and foliage size are established as an average using standard commercial cultural practices. Where terms such as medium, average, normal, etc. are used, the characteristics so described are not considered to be distinguishing.

Name: CFPC Sugarplum.

Classification:

*Botanical.*—*Dianthus caryophyllus.*

*Commercial.*—Carnation, dwarf, pot type.

Parentage:

*Female parent.*—'Peachy'.

*Male parent.*—'Claret Elegance'.

PLANT

Height: About 8 inches.

Growing habit: Herbaceous, semi-upright, pot plant.

Blooming habit: As a spray.

Blooming season: Year round.

Rooting time: About 13 days.

Mutation prone: No.

Disease resistance: Fair, No disease problems noted.

Temperature tolerance: 120° F. to 10° F.

Breaking action: Good, about 11 on average.

Foliage

Color:

*Upper side.*—Near 139A.

*Lower side.*—Near 139B.

Size: About 3½ inches.

Quantity: Numerous.

Shape: Lanceolate.

Texture: Smooth.

Ribs: Central, Keeled.

Arrangement: Bi-lateral along stem.

Stem color: Green.

Bud

Shape: Ovoid.

Color: Green.

Length: About ¾-inch.

Diameter: About ¼-inch.

Calyx

Number of sepals: About 5.
Length: About ½-inch.
Width: About ¼-inch.
Color: Outside — near 143B. Inside — near 144D.

Bloom

Shape: Round.
Size:
*Diameter average.*—About 2-inches.
*Depth average.*—About 1-inch.
Borne: As a spray.
Color:
*General tonality.*—Purple flushed lavender.
*Upper side.*—Near 69A.
*Lower side.*—Near 74B.
*Center.*—Near 74A to 74B.
*Outer petals.*—Near 67B.
Keeping quality: Good, 3 to 4 weeks on plant.
Fragrance: Very Strong.

PETALS

Number: About 38.
Outer petals:
*Length.*—About 1-inch.
*Width.*—About ½-inch.
Central Petals:
*Length.*—About ½-inch.
*Width.*—About ¼-inch.
Texture: Smooth.
Form: Fan shaped.

Appearance: Shiny.

Reproductive organs

Stamens:
*Number.*—About 10.
*Arrangement.*—Around the ovary.
Anthers:
*Length.*—About 1/10-inch.
*Color.*—Near 70B.
Filaments:
*Length.*—About ½-inch.
*Color.*—Near to 157D.
Pistil:
*Number.*—About 2.
*Color.*—Near 57A.
*Length.*—About ¼-inch.
Stigma:
*Number.*—About 2.
*Color.*—Near 59A.
Ovary:
*Shape.*—Conical.
*Color.*—Base — green. Body — green. Apex — tan.
Fertility:
*As female and male.*—Extremely poor.

I claim:

1. A new and distinct variety of dwarf carnation plant named 'CFPC Sugarplum', substantially as shown and described.

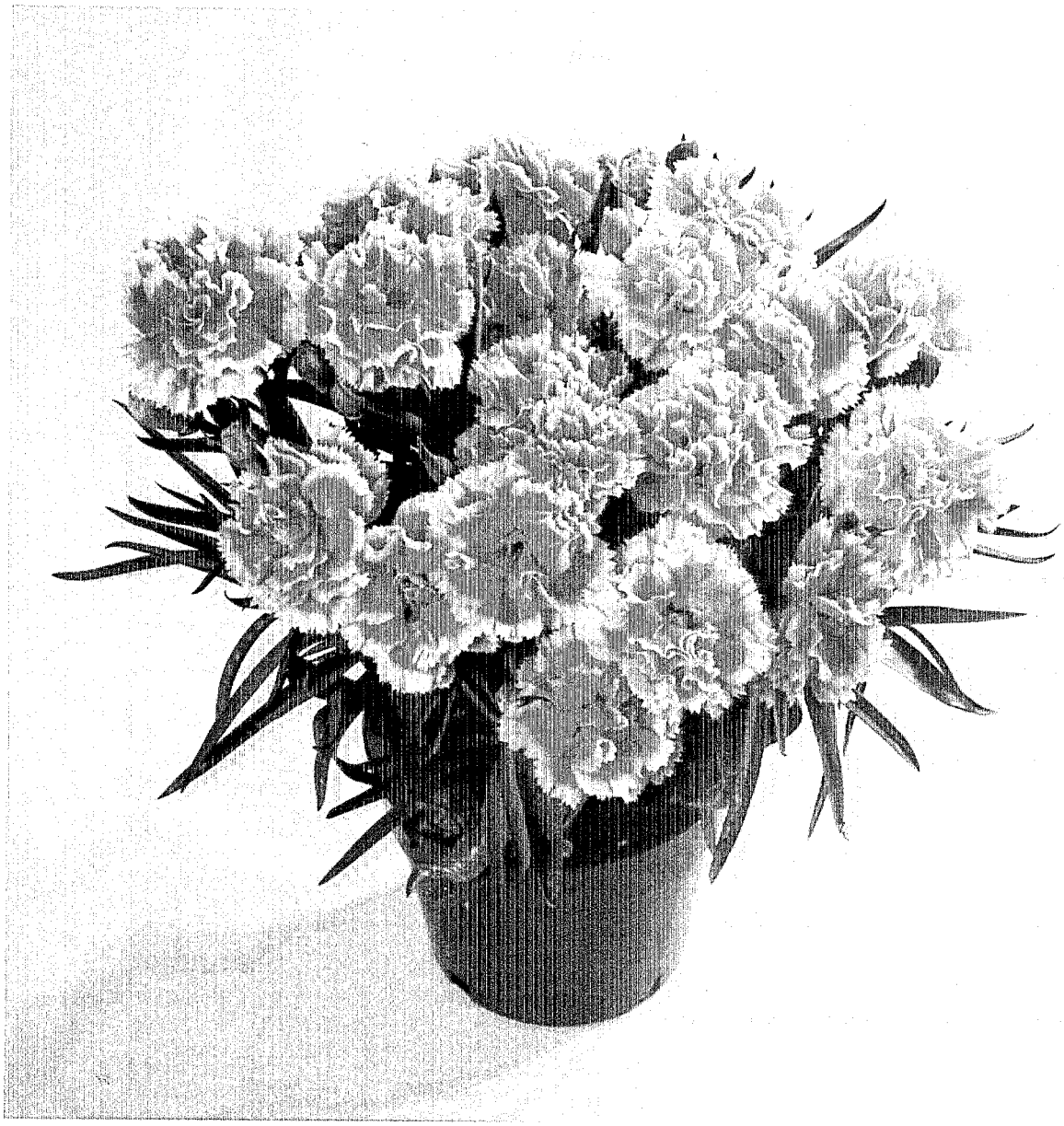

* * * * *